(12) United States Patent
Gleason et al.

(10) Patent No.: US 6,280,959 B1
(45) Date of Patent: *Aug. 28, 2001

(54) METAL COMPLEXES

(75) Inventors: John G. Gleason, Downingtown; Juan I. Luengo, Audubon, both of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,307
(22) PCT Filed: Oct. 30, 1998
(86) PCT No.: PCT/US98/23186
    § 371 Date: Apr. 27, 2000
    § 102(e) Date: Apr. 27, 2000
(87) PCT Pub. No.: WO99/22732
    PCT Pub. Date: May 14, 1999

Related U.S. Application Data
(60) Provisional application No. 60/063,957, filed on Oct. 31, 1997.

(51) Int. Cl.$^7$ ............................ G01N 33/53; C12Q 1/00
(52) U.S. Cl. .................................... 435/7.1; 435/4
(58) Field of Search ........................... 435/4, 7.1

(56) References Cited
U.S. PATENT DOCUMENTS

| 5,693,515 | 12/1997 | Clark et al. | 435/184 |
| 5,767,078 | 6/1998 | Johnson et al. | 514/12 |
| 5,773,569 | 6/1998 | Wrighton et al. | 530/300 |
| 5,830,851 | 11/1998 | Wrighton et al. | 514/2 |
| 5,869,451 | 2/1999 | Dower et al. | 514/13 |
| 5,981,551 | 11/1999 | Luengo et al. | 514/333 |

FOREIGN PATENT DOCUMENTS

| 9217200 | * 12/1992 | (WO). |
| WO 99/22732 | 5/1999 | (WO). |
| WO 99/22734 | 5/1999 | (WO). |

OTHER PUBLICATIONS

Botros et al., "Immobilized metal ion affinity partitioning of cells in aqueous two–phase systems:erythrocytes as a model", *Biochimica et Biophysica Acta*, 1074, pp. 69–73 (1991).

Arai et al., "Bleomycin Model Complex Bearing A Carbamoyl Derived Substituent Capable of Coordination to the Chelated Metal Ion As A Sixth Ligand", *Bioorganic & Medicinal Chemistry Letters*, 7(1), pp. 15–18 (1997).

Rao et al., Technetium(V) and Rhenium(V) Complexes of 2,3–Bis(mercaptoacetamido) propanoate. Chelate Ring Stereochemistry and Influence on Chemical and Biological Properties, *J. Am. Chem. Soc.*, 112 pp. 5798–5804 (1990).

Katz et al., "Design of potent selective zinc–mediated serine protease inhibitors", *Letters to Nature*, 391, pp. 608–613 (1998).

Bergeron et al., "Synthesis and Biological Evaluation of Naphthyldesferrithiocin Iron Chelators", *J. Med. Chem.*, 39, pp. 1575–1581 (1996).

(List continued on next page.)

Primary Examiner—Louise N. Leary
(74) Attorney, Agent, or Firm—Wayne J. Dustman; William T. King; Charles M. Kinzig

(57) ABSTRACT

The invention describes zinc chelated dimeric cell-surface receptor ligands, pharmaceutical compositions containing these compounds, methods of using these compounds as agonist of dimeric cell-surface receptors. Novel processes used in preparing the compounds are also described. Further, the invention describes novel receptor binding moieties of the zinc chelated cell-surface receptor ligands.

53 Claims, 5 Drawing Sheets

OTHER PUBLICATIONS

Chi et al., "Homodimeric and Heterodimeric Bis(amino thiol) Oxometal Complexes with Rhenium(V) and Technetium(V). Control of Heterodimeric Complex Formation and an Approach to Metal Complexes that Mimic Steroid Hormones",*J. Med. Chem.*, 37, pp. 928–937 (1994).

Wrighton et al., "Small Peptides as Potent Mimetics of the Protein Hormone Erythropoietin", *Science*, 273, pp. 458–463 (1996).

Cwirla et al., "Peptide Agonist of the Thrombopoietin Receptor as Potent as the Natural Cytokine",*Science*, 276, pp. 1696–1699 (1997).

Linvah et al., "Functional Mimicry of a Protein Hormone by a Peptide Agonist:The EPO Receptor Complex at 2.8A", *Science*,273, pp. 464–471 (1996).

Klekota et al., "Generation of Novel DNA–Binding Compounds by Selection and Amplification from Self–Assembled Combinatorial Libraries", *Tetrahedron Letters*, 38(50), pp. 8639–8642 (1997).

Chi et al., "Selective F ormation of Heterodimeric Bis–Bidentate Aminothiol–Oxometal Complexes of Rhenium(V)", *J. Am. Chem. Soc.*, 115, pp. 7045–7046 (1993).

Routier et al., "Salen–Anthraquinone Conjugates. Synthesis, DNA–Binding and Cleaving Properties, Effects on Topoisomerases and Ctotoxicity", *Bioorganic & Medicinal Chemistry*, 4(8), pp. 1185–1196 (1996).

\* cited by examiner

METAL COMPLEXES

This Appln claims benefit of Provisional Appln No. 60/063,957 filed Oct. 31, 1992.

FIELD OF THE INVENTION

This invention relates to metal complexed receptor ligands, methods for making and identifying them and their use as agonist of dimeric receptors. More specifically, the invention describes a method to promote the oligomerization of dimeric receptors.

BACKGROUND OF THE INVENTION

Many soluble proteins, such as cytokines, hormones and growth factors, exert their functions by binding and activating cell-surface receptors (Arai, K.-I. et al. Annu. Rev. Biochem. 1990, 59, 783; Bazan, J. F. Proc. Natl. Acad. Sci. U.S.A. 1990, 87, 6934; Ullrich A. and Schiessinger, J. Cell, 1990, 61, 203–212). These receptors are comprised of three distinct domains: an extracellular ligand-binding domain, a transmembrane domain and a cytoplasmic domain, which is responsible for signal transduction within the cell. Some receptors, such as those for erythropoietin (EPO), thrombopoietin (TPO), and granulocyte-colony stimulating factor (G-CSF), contain the ligand-binding and signal-transduction domains within the same polypeptide subunit. Others, such as receptors for interleukin-2 (IL-2), IL-3 and IL-6 have separate components for ligand-binding and signal transduction. Although the mechanism of receptor activation varies for specific receptor-ligand pairs, a common feature of many single-transmembrane receptors appears to be their aggregation on the cell membrane in response to binding of their specific ligands. This aggregation event can be in the form of homodimerization, in the case of receptors with a single subunit, or heterodimerization, in the case of receptors with different subunits. It has become clear that receptor aggregation is part of the biological signal by which the target cell responds to the presence of specific hormones and growth factors (Young, P. R. "Protein hormones and their receptors", Curr. Opin. Biotech. 1992, 3, 408–421; Heldin, C. H., "Dimerization of cell surface receptors in signal transduction). Typical examples of such receptors are growth factor receptors with tyrosine kinase activity as well as cytokine receptors.

Monoclonal antibodies have been discovered which have agonist activity to the dimeric receptors such as those from epidermal growth factor (EGF, Fernandez-Pol, J. J. Biol. Chem. 1985, 260,5003–11; Serrero, G. U.S. Pat. No. 5,723, 115), G-CSF (Takahashi, T. et al. J. Biol. Chem. 1996, 271, 17555–17560), tumor necrosis factor (TNF, Fine, S. M. et al. J. Biol. Chem. 1996, 27126, 15303–15306.), growth hormone receptor (Rowlinson, S. W. et al. J. Biol. Chem. 1998, 2739, 5307–5314, EPO (Young, P. R. and Erickson-Miller, C. L. WO 9640231; Chaovapong, W. L. et al. WO 9748729.) and gp130, the common chain for members of the IL-6 family (Fourcin, M. et al. J. Biol. Chem. 1996, 271, 11756–11760). Ability of the monoclonal antibodies to activate the receptors is believed to be due to the presence of the two antigen binding sites, which can bridge the two receptor subunits and facilitate aggregation.

More recently peptides with agonist activity were identified by screening of phage display libraries against the EPO (Wrighton, N. C. et al. Science 1996, 273, 458–463; Wrighton, N. C. et al. U.S. Pat. No. 5,773,569) and TPO receptors (Cwirla, S. E. et al. Science 1997, 276, 1696–1699; Dower, W. J. et al. WO 9640750). The peptides ranged from 14 to 20 residues and activated the receptors by promoting their dimerization on the cell surface. These agonist peptides are unrelated to EPO and TPO and appear to act as dimeric agents, as demonstrated in the crystal structure of the EMPI/EBP complex (Livnah, O. et al. Science 1996, 273,464–471).

Despite the success of monoclonal antibodies and dimeric peptides in eliciting agonist response in certain dimeric receptors, they are not generally considered desirable candidates for development of pharmaceutical compositions. Lack of oral bioavailability and a limited serum half-life limit the desirability and efficacy of monoclonal antibodies and polypeptides as pharmaceutical agents. Consequently, a need exists for non-antibody ligands which have agonist properties towards dimeric cell-surface receptors.

Notwithstanding the fact that these receptors have been the subject of such research efforts for over a decade, only one application (PCT/US97/08,864) describes small organic molecules which exhibit agonist activity towards dimeric cell-surface receptors. This application does not mention zinc chelated small organic molecules.

As disclosed herein it has unexpectedly been discovered that zinc chelated receptor ligands have agonist properties towards dimeric cell-surface receptors.

SUMMARY OF THE INVENTION

Accordingly, one aspect of the present invention is a method for agonizing dimeric cell-surface receptors which comprises contacting the receptor with a zinc chelated receptor ligand.

Another aspect of the invention is a method for identifying agonists of dimeric cell-surface receptors.

A third aspect of the invention relates to zinc chelated dimeric cell-surface receptor ligands.

A fourth aspect of the invention relates to an isolated receptor binding moiety of a zinc chelated dimeric cell-surface receptor ligand.

A fifth aspect of the invention is a method for making zinc chelated dimeric cell-surface receptor ligands.

BRIEF DESCRIPTION OF THE DRAWINGS

FIG. 2 shows the same type of experiment in NFS60 cells, but run in the presence of 1 uM zinc (II). The activity of compound 1a is about 350% over control, which indicates that zinc(II) potentiates the activity of compound 1a.

DETAILED DESCRIPTION OF THE INVENTION

Figure 1:
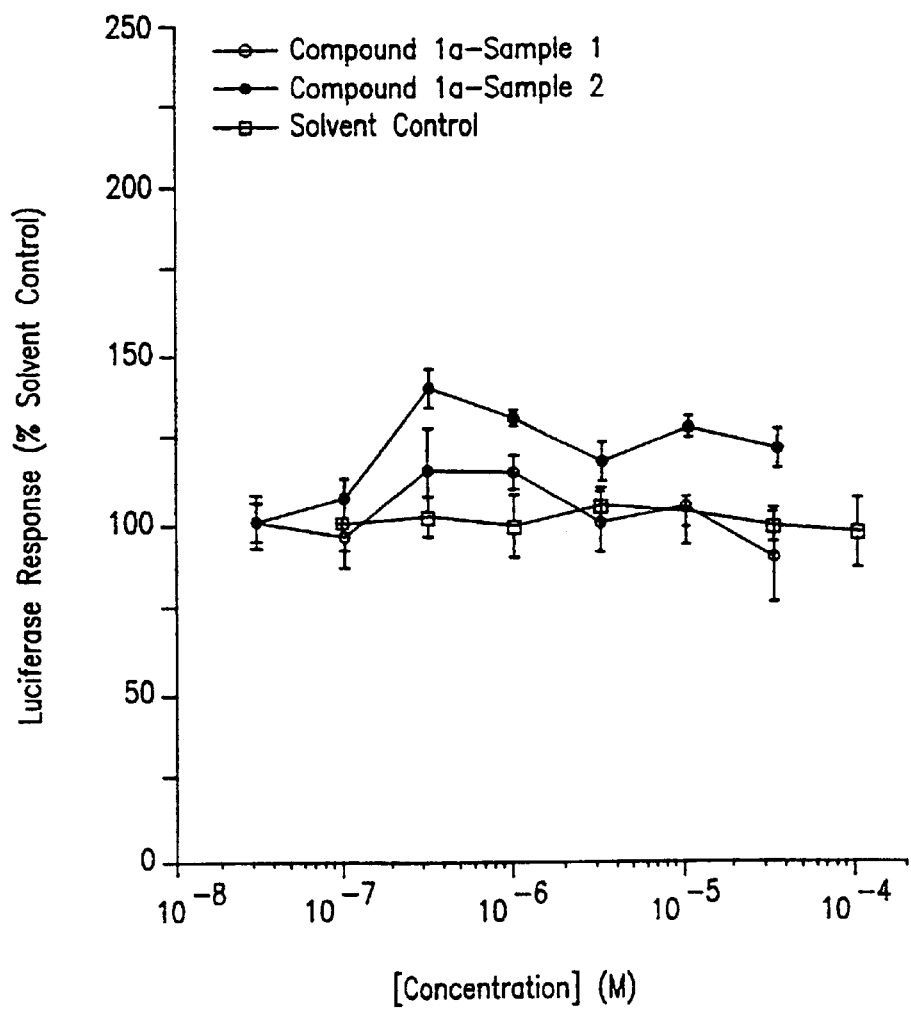
FIG. 1 shows the activity of two different samples of compound 1a (from Example 1) on the murine myeloid cell line NFS60 that contained a G-CSF-responsive element linked to a minimal promoter and the gene for luciferase. Activity of compound 1a is below the threshold of 150% over background. The study was performed as a Luciferase assay configured on the G-CSF-responsive NFS60 cell line as described in Tian et al., Science 281, 257–259 (1998). The experiments shown in FIGS. 2–8 used the same NFS60 cell line.

All publications, including but not limited to patents and patent applications, cited in this specification are herein incorporated by reference as though fully set forth.

By the term "heteroatom(s)", as used herein is meant nitrogen, oxygen or sulfur, preferably nitrogen.

By the term "treating" and derivatives thereof as used herein, is meant prophylatic or therapeutic therapy.

By the term "organic molecule" and derivatives thereof as used herein, is meant the standard usage in the art to the ordinary organic chemist and as such excludes inorganic molecules and peptide molecules.

The zinc chelated receptor ligands of this invention that have agonist properties towards dimeric cell-surface receptors are compounds that consist of one or more receptor binding moieties, preferably 1 to 4 moieties, most preferably 1 or 2 moieties, wherein each receptor binding moiety forms at least two coordinate bonds to each of one or more zinc ions, preferably each moiety will form two or three coordinate bonds to each of one or two zinc ions.

By the term "receptor binding moiety", and derivatives thereof, as used herein means a small organic molecule having a molecular weight from about 100 to about 850, preferably having a molecular weight from about 200 to about 750, most preferably having a molecular weight from about 300 to about 650 and having from 1 to 4 zinc binding motifs, preferably having one or two zinc binding motifs. In one embodiment, metal chelation forms a symmetrical multimer, such as a dimer, of the receptor binding moiety.

By the term "zinc binding motif", and derivatives thereof, as used herein means a continuation of atoms within a receptor binding moiety that have the following characteristics:

1) each continuation consist of 3 to 10 atoms, preferably 4 to 8 atoms, most preferably 4 or 5 atoms,
2) each continuation further consisting of two or more heteroatoms, preferably from 2 to 4 heteroatoms, most preferably 2 to 3 heteroatoms, preferably at least one of the heteroatoms is nitrogen, wherein the heteroatoms are separated from each other by one to four additional atoms selected from the group consisting of carbon, nitrogen, sulfur and oxygen, preferably carbon or nitrogen, preferably by 2 to 4 additional atoms, most preferably by 2 or 3 additional atoms, and
3) the configuration of heteroatoms within the zinc binding motif allows for chelate coordination to a zinc (II) ion by providing for the formation of at least two coordinate bonds, preferably two or three coordinate bonds, simultaneously to a zinc ion.

Examples of zinc binding motifs for use in the present invention include but are not limited to the following: —N—C—C—N—, —N—C=C—N—, —N—C—C=N—, —N=C—C=N—, —O—C—C—N—, —O—C=C—N—, —O—C—C=N—, —O=C—C=N—, —S—C—C—N—, —S—C=C—N—, —S—C—C=N—, —S=C—C=N—, —S—C—C—S—, —N=—C—N—N—, —N—C—N—N—, —O c—N—N—, —S=C—N—N—, —C—C—C=O—, —O—N—C=O—, —N=C—N—C=N—, —O=C—N—C=N—, —N=C—C—C=N—, —O—=C—C—=O—, —N—C—C—C—N—, —N—C—C=C—N—, —N=C—C=C—N—, —N=C—C=C—O—, —N=C—C=C—S—, —S=C—C=C—S—, —O=C—N—C=N—, —N—N—C—C=N—, —N—N—C—C—N—, —N—C=N—C=N—, —N=C—N—C=N—C—N— and —N=C—N—C=N—C—C=N—.

Preferred receptor binding moieties of the present invention comprise one or more of the following functional groups, preferably one or two of the following functional groups: 2-guanidinobenzimidazoles, 2-guanidinobenzoxazoles, 2-guanidionbenzothiazole, 2-mercaptomethylpyridines, acylacetones, acylhydrazines, 2-aminoethanethiols, 2-(imidazol-4-yl)ethylamines, 2-(imidazol-2-yl)ethylamines, 2-(imidazol-4-yl)ethylimines, 2-(imidazol-2-yl)ethylimines, 2-picolylamine, 8-hydroxyquinolines. 8-aminoquinolines, 8-mercaptoquinolines, ethylenediamines, pyridine-2-carboxaldimines, 2,2'-bipyridyls, 2-thiobenzaldimines, 2-hydroxybenzaldimines and 2,5-diimino-3a,6a-diaryl-1,2,3,3a,4,5,6,6a-octahydroimidazo[4,5-d]imidazoles.

The above functional groups will generally form part of a larger molecule and may be further substituted in the formation of a receptor binding moiety. Preferred substituents for optional use on the above functional groups consist of one or more groups selected from the following: alkyl, aryl, hydroxy, alkoxy, acyloxy, carbamoyl, amino, N-acylamino, ketone, halogen, cyano, thio, carboxy and carboxamido.

As noted from the depiction of bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II) in Example 1 below, an 8 atom zinc binding motif (specifically the —N=C—N—C=N—C—C=N—) is essentially an overlap of a 5 atom zinc binding motif (that is —N=C—N—C=N—) and a 4 atom zinc binding motif (that is —N—C—C=N—) in a continuation. As such, preferred zinc binding motifs of the instant invention consist of a continuation of 4 or 5 atoms either individually or as part of a combination. Further, each atom of a zinc binding motif of the present invention may be further substituted, may be saturated or contain various degrees of unsaturation or may form part of a larger linear system or an aromatic or nonaromatic ring system.

The zinc chelated receptor ligands of this invention are included in the pharmaceutical compositions of the invention and used in the methods of the invention. The receptor binding moieties of this invention are included in the pharmaceutical compositions of the invention and used in the methods of the invention.

By the term "co-administering" and derivatives thereof as used herein is meant either simultaneous administration or any manner of separate sequential administration of a zinc chelated receptor ligand, as described herein, and a further active ingredient or ingredients. For example, antibacterial agents or antifungal agents. Preferably, if the administration is not simultaneous, the agents are administered in a close time proximity to each other. Furthermore, it does not matter if the agents are administered in the same dosage form, e.g. one agent may be administered subcutaneously and another agent may be administered orally.

The zinc chelated receptor ligands of this invention are prepared by reacting one or more receptor binding moieties and a zinc ion source, such as $Zn(NO_3)_2$, in a solvent, followed by optional isolation of the zinc chelated receptor ligand. The order in which the indicated ingredients are utilized in the presently invented process is not critical. All orders of addition of the indicated ingredients are within the scope of the invention. Further, the zinc chelated receptor ligands of this invention can be prepared in vivo by the administration of a receptor binding moiety to a subject and utilization of naturally occurring zinc ions in the body of the subject.

Pharmaceutically acceptable salts, hydrates and solvates are formed when appropriate by methods well known to those of skill in the art.

Because the pharmaceutically active compounds of the present invention are active as agonist of dimeric cell-surface receptors they exhibit therapeutic utility in treating disease states associated with compromised function of such dimeric cell-surface receptors. For example, a zinc chelated G-CSF receptor agonist would exhibit efficacy in treating bacterial infections, fungal infections, neutropenia, including chemotherapy-induced neutropenia and bone marrow transplantation and in mobilizing peripheral blood stem cells and other conditions with depressed leukocyte production.

In determining the potency of the presently invented compounds as agonist of dimeric cell-surface receptors, the following assays are employed:

Luciferase Assay

Compounds of the present invention are tested for potency as agonist of a dimeric cell-surface receptor in a Luciferase reporter gene assay such as described in Tian et al., *Science* 281, 257–259 (1998). For example, for G-CSF NFS60 cells (Holmes, et al., *Proc. Natl. Acad. Sci.* USA 82: 6687–6691 (1985)) are selected because they express endogenous G-CSF receptors closely matching the pattern of STAT (signal transducers and activators of transcription) activation observed in primary murine and human bone marrow cells.

Luciferase Assay and EDTA

In order to determine the requisiteness of zinc chelation of small organic molecules to agonist activity at dimeric cell-surface receptors, the above luciferase assay was performed on the G-CSF receptor in the presence of EDTA. EDTA is a strong metal chelator and had as its only effect, the removal of zinc from the ligand-receptor interaction.

CFU-G Assay

Compounds of this invention are also tested for activity in the following assays: CFU-G assay (an example of which is described in King A G, Talmadge J., Badger A M, Pelus L M. Regulation of colony stimulating activity production from bone marrow stromal cells by the hematoregulatory peptide, HP-5. *Exp. Hematol.* 20:223–228, 1992) and in vivo evaluation of peripheral blood neutrophil and monocyte count in the mouse (an example of which is described in Pelus, L. M.; King, A. G.; Broxmeyer, H. E.; DeMarsh, P. L.; Petteway, S. R.; Bhatnagar, P. K., *In vivo modulation of hematopoiesis by a novel hematoregulatory peptide* Exp-Hematol. 1994 22(3): 239–47). In order to confirm the requirement for zinc(II) chelation, the above CFU-G assay was also conducted in the presence of EDTA.

Isothermal Titration Microcalorimetry

Zinc-mediated affinity of compounds from this invention for dimeric cell-surface receptors (specifically the G-CSF receptor) was measured by isothermal titration microcalorimetry experiments. Titration microcalorimetry detects binding as heat originating from the intrinsic bond forming enthalpy change. In this assay, the compounds were titrated first against zinc(II) alone. In a separate experiment, the compounds were then assayed in the presence of zinc and a dimeric cell-surface receptor/Fc fusion protein (a G-CSF/Fc fusion protein), which contained the extracellular domain of the receptor presented in a dimeric form due to the Fc component. Interaction with the fusion protein construct was confirmed from the binding enthalpy change, which was substantially increased over that of zinc alone. When the latter experiment was carried out in the absence of zinc, no heat of binding was detected, indicating that no interaction with the fusion protein construct occurred under those conditions.

Compounds 1a and 3a bind to the fusion protein construct with high, submicromolar affinity only in the presence of zinc. Compounds 1, 1a, 2a, and 3a showed activation above 150% of control between the concentration range of 1 to 100 micromolar in the luciferase assay. Further, compound 1a and 3a showed activation above 150% of control between the concentration range of 1 to 100 micromolar in the murine assay. Compounds 1a and 3a showed elevation of peripheral blood neutrophil and monocyte count in the mouse.

Figure 2:
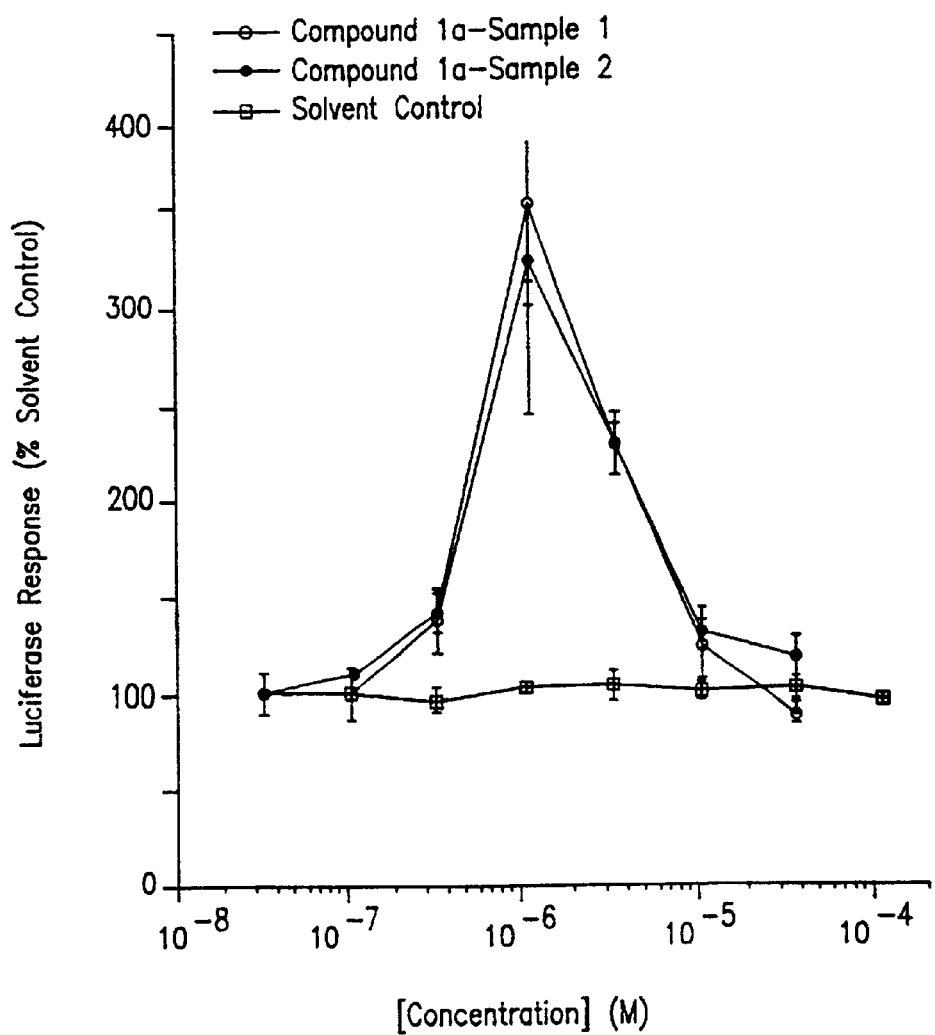

As demonstrated by the results depicted in FIG. 1, the agonist activity of Compound 1a in the absence of zinc is below the activity threshold of 150% over background. However, as shown in FIG. 2, the presence of 1 uM zinc(II) activates compound 1a, so that it becomes an agonist of the dimeric cell-surface receptor with an efficacy of 350% over background at 1 uM. This is an indication that zinc(II) mediates the activity of compound 1a.

Figure 3:
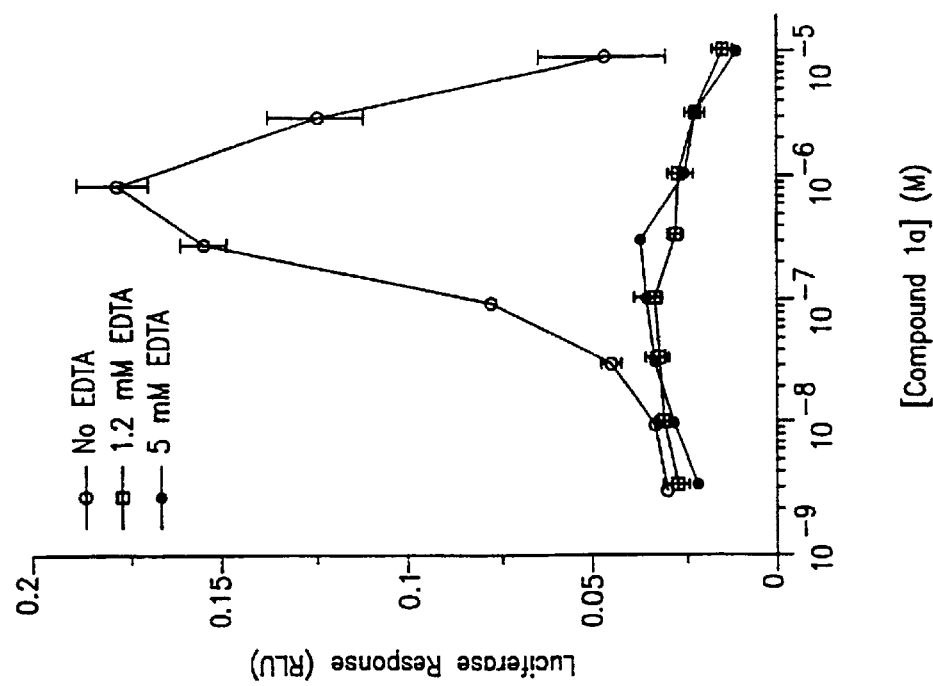
FIG. 3 is an analysis of the effect of ethylenediaminetetraacetic acid (as used herein—EDTA) on the activity of Compound 1a (from Example 1) in NFS60 cells. Shown are luciferase response curves of Compound 1a at the indicated concentrations and in the presence of various concentrations of EDTA. EDTA at 1.2 millimolar concentration antagonized the activity of compound 1a. The media in this assay contained a small amount (1–5 uM) of zinc(II).

As demonstrated by the results depicted in FIG. 3, the agonist activity of Compound 1a was abrogated in the presence of EDTA, confirming that a metal ion mediates the activity.

Figure 4:
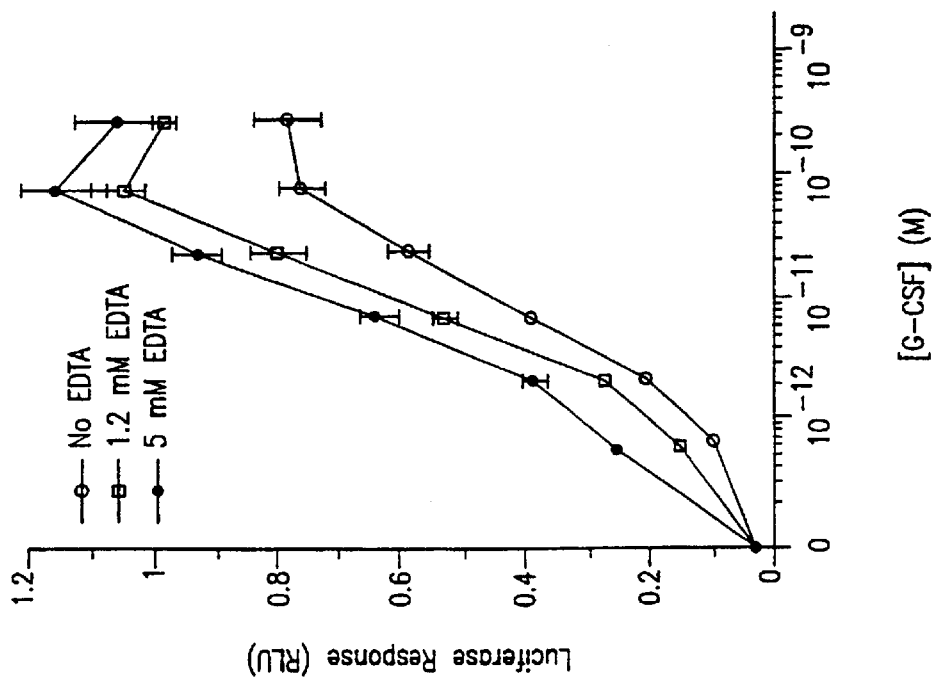
FIG. 4 is an analysis of the effect of EDTA on the activity of recombinant G-CSF on NFS60 cells. Shown are luciferase response curves of recombinant G-CSF at the indicated concentrations and in the presents of various concentrations of EDTA. EDTA at both 1.2 and 5 millimolar has little effect on the activity of recombinant G-CSF in the assay.

Conversely, the results depicted in FIG. 4 indicate that the agonist activity of the natural ligand (i.e. G-CSF or recombinant G-CSF as demonstrated herein) is not mediated by metal ions.

Figure 6:
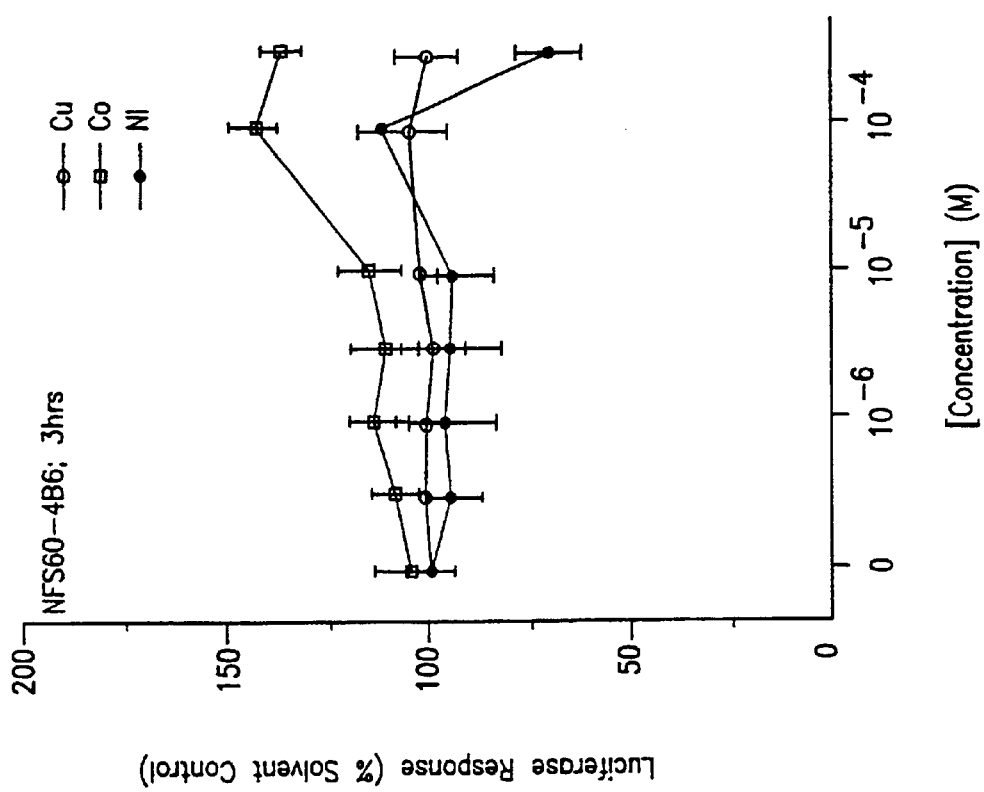
FIGS. 5 and 6 depict an analysis of the activity of metal chlorides alone on the basal luciferase level of NFS60 cells. Shown are luciferase response curves of the indicated metal chlorides at various concentrations. None of the metals have a meaningful effect on the basal luciferase levels at concentrations equal or less than 10 micromolar.
Figure 5:
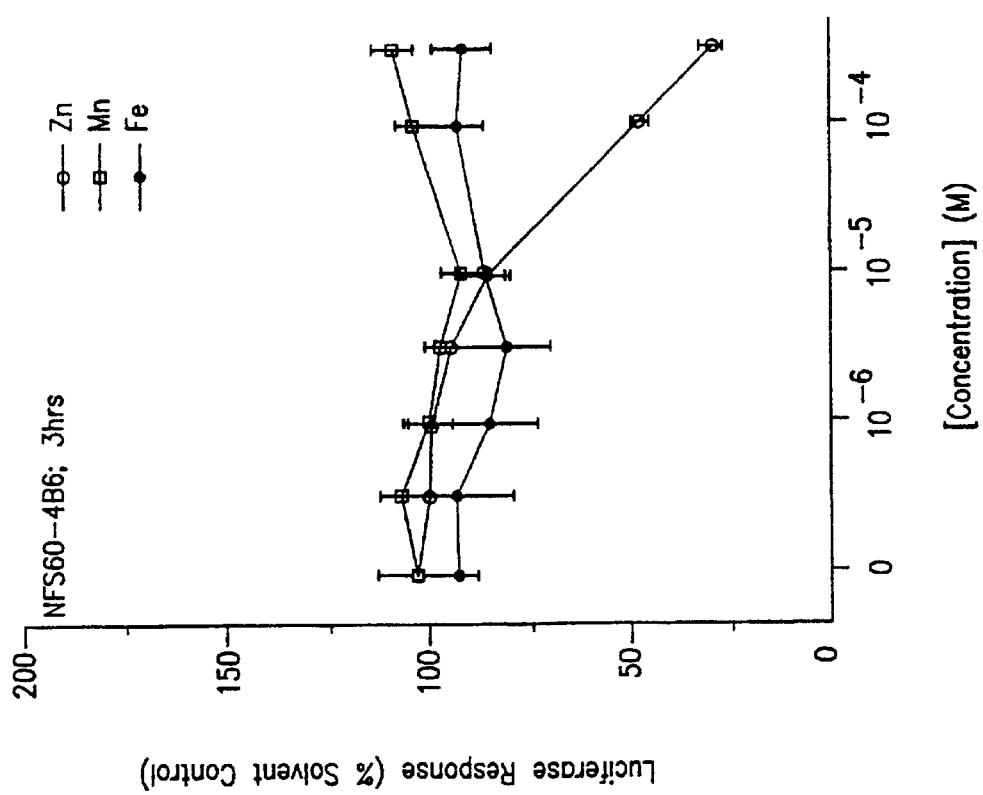

The results depicted in FIGS. 5 and 6 indicate that metal ions alone are insufficient to trigger an agonist response at a dimeric cell-surface receptor.

Figure 8:
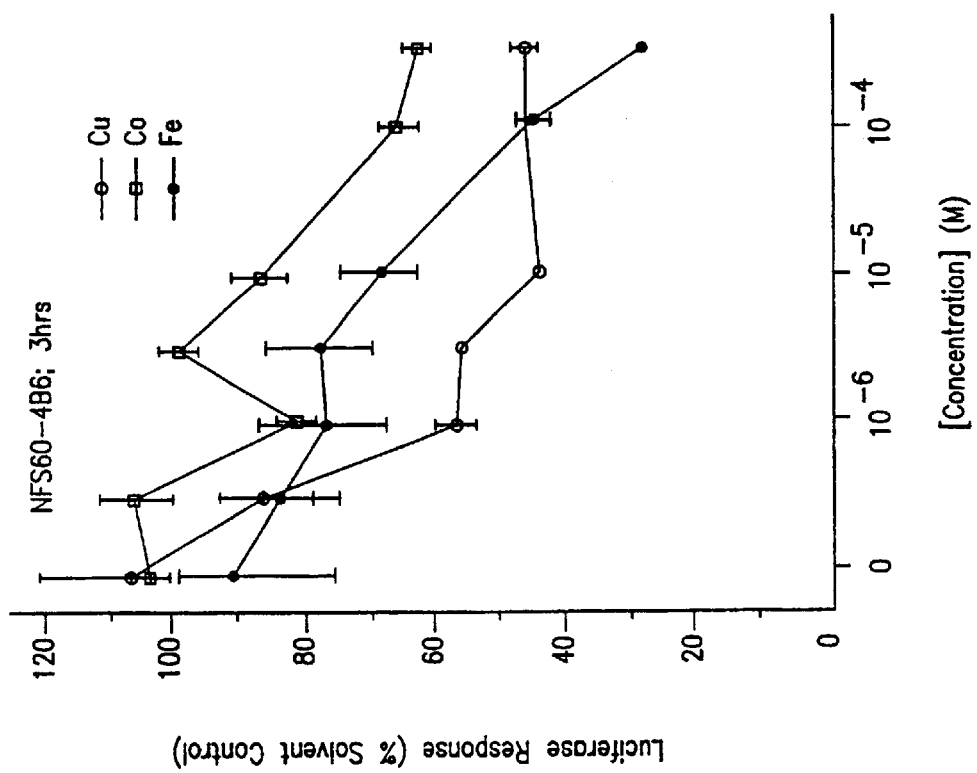
FIGS. 7 and 8 show an analysis of the effect of metal chlorides on the EDTA depleted activity of Compound 1a on NFS60 cells. Shown are luciferase response curves as effected by the indicated metal chlorides. Only zinc (II) at concentrations 0.5–10 micromolar can overcome the inhibition in luciferase activity caused by 50 micromolar concentration of the metal chelator EDTA. None of the other metals tested could overcome the inhibitory effect of EDTA.
Figure 7:
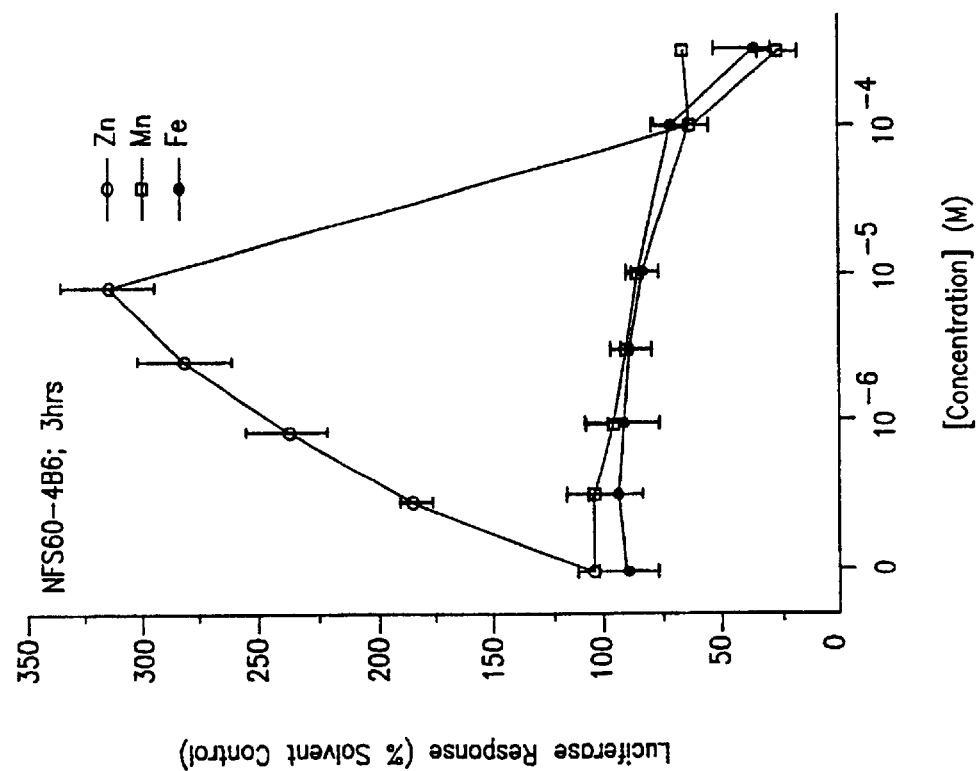

The results depicted in FIGS. 7 and 8 indicate that chelation of a small molecule to zinc ions (and not ions of manganese, iron, copper or cobalt) is a requirement for activation of the dimeric cell-surface receptor by organic molecules.

The results depicted in FIGS. 1 through 8 demonstrate, for the first time, that zinc chelated small molecules, or zinc chelated receptor ligands as used herein, are necessary for activation of dimeric cell-surface receptors by organic molecules.

Based on the description in the specification and in the Examples one of skill in the art can readily design and prepare a zinc chelated dimeric cell-surface receptor ligands. Further, one of skill in the art can readily determine if a dimeric cell-surface receptor ligand candidate is acting as an agonist of the receptor by using the assays described herein and then repeating the experiments of FIGS. 1 through 8.

The pharmaceutically active compounds within the scope of this invention are useful as dimeric cell-surface receptor agonist in mammals, including humans, in need thereof.

The present invention therefor provides a method of treating disease states associated with compromised function of dimeric cell-surface receptors, which comprises administering a zinc chelated receptor ligand in a quantity effective to enhance receptor activation. For example, a zinc chelated G-CSF receptor agonist would exhibit efficacy in treating bacterial infections, fungal infections, neutropenia, including chemotherapy-induced neutropenia and bone marrow transplantation and in mobilizing peripheral blood stem cells and other conditions with depressed leukocyte production, through the administration of a zinc chelated G-CSF receptor ligand in a quantity effective to enhance leukocyte production. The zinc chelated receptor ligands of the present invention also provide for a method of treating the above indicated disease states because of their demonstrated ability to act as agonist of dimeric cell-surface receptors. The drug may be administered to a patient in need thereof by any conventional route of administration, including, but not limited to, intravenous, intramuscular, oral, subcutaneous, intradermal, and parenteral. Also, the drug may be formed in vivo by the administration of a dimeric cell-surface receptor binding moiety (or receptor binding moiety as used herein) by the same methods of administration described herein and in about the same amounts as described herein for zinc chelated receptor ligands. Further, the possibility exists that solubility and bioavailability concerns will be associated with the zinc chelated receptor ligands of the present invention. Thus, depending on the particular moiety in question, it will often be preferable to administer a receptor binding moiety of the present invention and thereinby subsequently form a zinc chelated receptor ligand in vivo using plasma as the solvent and naturally occurring zinc ions. It is also contemplated herein that a receptor binding moiety of the present invention be administered with a zinc source so as to facilitate the in vivo formation of a zinc chelated receptor ligand.

The pharmaceutically active zinc chelated receptor ligands of the present invention or, when desired and appropriate, the receptor binding moieties of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin. agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingreidents, as appropriate, to give the desired oral or parenteral products.

Doses of the presently invented pharmaceutically active zinc chelated receptor ligands of the present invention or, when desired and appropriate, the receptor binding moieties of the present invention, in a pharmaceutical dosage unit as described above will be an efficacious, nontoxic quantity preferably selected from the range of 0.001–125 mg/kg of active compound, preferably 0.001–60 mg/kg. When treating a human patient in need of an agonist of a dimeric cell-surface receptor, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular zinc chelated receptor ligand or receptor binding moiety in use, the strength of the preparation, the mode of administration, and the advancement of the disease condition. Additional factors depending on the particular patient being treated will result in a need to adjust dosages, including patient age, weight, diet, and time of administration.

Another aspect of the present invention is a method for identifying agonists of dimeric cell-surface receptors and receptor ligands identified thereby. In the method, the dimeric cell-surface receptor is contacted with receptor ligand candidates in the presence of a micromolar concentration of zinc(II). Ligand candidates which bind to the dimeric cell-surface receptor are selected by receptor binding assays well known to those skilled in the art, such as competitive and non-competitive binding measurements (*Immobilized Affinity Ligand Techniques*, G. T. Hermanson, A. K. Mallia, P. K. Smith Eds., Academic Press Inc. San Diego, Calif. 1992), isothermal microcalorimetry (*Rapid Measurement of Binding Constants and Heats of Binding Using a New Titration Calorimeter* T. Wiseman, S. Williston, J. F. Brandts, and L.-N. Lin (1989) *Analytical Biochemistry* 179, 131–137.), sedimentation equilibrium (T. Horan et al. *Biochemistry* 1996, 35, 4886–4896), ELISA, RIA methodologies (*An Introduction to Radioimmunoassays and Related Techniques*, T. Chard, Elsevier Science Publishers, Amsterdam, The Netherlands, 1990), BIAcore® (*BIAtechnology Handbook*, Pharmacia Biosensor AB, Uppsala, Sweden, 1994), fluorescence anysotropy methodology (*Luminesct Spectroscopy of Proteins*, E. A. Permyakov, CRC Press Inc., Boca Raton, Fla. 1992), flow cytometry technology (*Flow Cytometry and Cell Sorting*, A. Radbruch, Springer-Verlag, New York, N.Y. 1992).

In general, the dimeric cell-surface receptor in isolated, immobilized or cell-bound form is contacted with a plurality of zinc chelated receptor ligand candidates and those candidates which bind to and interact with the receptor are selected. Optionally, the isolated, immobilized or cell-bound receptor is contacted with a variety of metal-chelating receptor ligand candidates in the presence of zinc(II). Binding interaction can be measured directly by using radioactively labeled ligand candidates or indirectly, by using cells expressing the dimeric cell-surface receptor and measuring the occurrence of an event mediated by the formation of a dimeric cell-surface receptor—ligand complex. Alternatively, the ligand candidates can be subjected to competitive binding assays in which the known receptor ligand, labeled preferably with an analytically detectable reagent, most preferably radioactivity, is included with the ligand candidates and a candidate's ability to inhibit the binding of the labeled ligand is measured.

Positive receptor ligand candidates are screened for biological function by any one of the receptor function assays well known to those skilled in the art. It is expected that a positive ligand binding candidate will exhibit agonist activity in receptor function assays.

An example of an appropriate competitive binding assay for the G-CSF receptor involves the immobilization of the G-CSF receptor and incubation with compounds of interest with $I^{125}$ radiolabeled G-CSF following the general procedure already described for other cytokine receptors (C. L. Martens et al. J. Biol. Chem. 1995, 270, 21129. E. Whitehorn et al. Biotechnology 1995, 13, 1215, S. D. Yanofsky et al. Proc. Natl. Acad. Sci. U.S.A. 1996, 93, 7381, N. C. Wrighton et al. Science, 1996, 273, 458, S. E. Cwirla, Science, 1997, 276, 1696).

The method of this invention of inducing agonist activity at a dimeric cell-surface receptor in mammals, including humans, comprises administering to a subject in need of such activity an effective amount of a pharmaceutically active zinc chelated receptor ligand of the present invention or, when desired and appropriate, a receptor binding moiety of the present invention.

The invention also provides for the use of a presently invented zinc chelated receptor ligand or a presently invented receptor binding moiety in the manufacture of a medicament for use as an agonist of a dimeric cell-surface receptor.

The invention also provides for the use of a zinc chelated receptor ligand or a receptor binding moiety in the manufacture of a medicament for use in therapy.

The invention also provides for the use of a zinc chelated receptor ligand or a receptor binding moiety in the manufacture of a medicament for use in enhancing the activity of a dimeric cell-surface receptor.

The invention also provides for the use of a zinc chelated receptor ligand or a receptor binding moiety in the manufacture of a medicament for use in treating disease states associated with compromised dimeric cell-surface receptor activity. For example, bacterial and fungal infections.

The invention also provides for a pharmaceutical composition for use as an agonist of a dimeric cell-surface receptor which comprises a zinc chelated receptor ligand or a receptor binding moiety and a pharmaceutically acceptable carrier.

The invention also provides for a pharmaceutical composition for use in treating bacterial infections which comprises a zinc chelated receptor ligand or a receptor binding moiety and a pharmaceutically acceptable carrier.

The invention also provides for a pharmaceutical composition for use in treating fungal infections which comprises a zinc chelated receptor ligand or a receptor binding moiety and a pharmaceutically acceptable carrier.

The invention also provides for a process for preparing a pharmaceutical composition containing a pharmaceutically acceptable carrier or diluent and a zinc chelated receptor ligand or a receptor binding moiety which comprises bringing the zinc chelated receptor ligand or the receptor binding moiety into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat disease states associated with compromised dimeric cell-surface receptor activity. For example, compounds to treat bacterial infections and fungal infections.

As indicated above, the zinc chelated compounds of the invention are utilized as agonists of cell-surface receptors whose signal transduction mechanism involves receptor dimerization or oligomerization. These receptors are divided in five superfamilies (reviewed by Heldin, C. H. *Dimerization of Cell Surface Receptors in Signal Transduction*, Cell 1995, 80, 213) as follows: protein-tyrosine kinase receptors (PDGFR-α, PDGFR-β, SCFR, CSF-R, Flk-2, EGFR, Erb2, Erb3, Erb4, FGFR-1, FGFR-2, FGFR-3, FGFR-4, insuline R, IGF-1R, HGFR, MSPR, Flt-1, Flk-1, Trk, TrkB, TrkC, Eph, Elk, Eck, Cck5, Sek, Eck, Erk), cytokine receptors (GHR, TPOR, EPOR, PRLR, G-CSFR, leptin R, IL-3R, GM-CSFR, IL-5R, IL-6R, LIFR, CNTRFR, IL-11R, IL-2R, IL-4R, IL-7R, IFN-α, IFN-β, IFN-γ, IL-10R), TNF receptors (TNFR, LGNFR, CD40, OX-40, Fas, CD27, CD30), antigen receptors (TCR, BCR) and serine/threonine kinase receptors (TGF-βR, ActR-II).

With regards to the presently invented subject matter, the term dimeric cell-surface receptor(s) refers to the receptors of the five superfamilies as listed above, with the exception of the G-CSF receptor.

In a further aspect of the invention, the zinc chelated compounds of the invention are utilized as agonist of the erythropoietin (EPO) receptor. Additionally, a therapeutically effective amount of a receptor binding moiety of the invention is administered to a subject in need of treatment for anemia.

In a further aspect of the invention, the zinc chelated compounds of the invention are utilized as agonist of the macrophage-colony-stimulating factor (M-CSF) receptor. Additionally, a therapeutically effective amount of a receptor binding moiety of the invention is administered to a subject in need of treatment for neutropenia.

In a further aspect of the invention, the zinc chelated compounds of the invention are utilized as agonist of the growth hormone (GRH) receptor. Additionally, a therapeutically effective amount of a receptor binding moiety of the invention is administered to a subject in need of treatment for growth hormone deficiency.

In a further aspect of the invention, the zinc chelated compounds of the invention are utilized as agonist of the thrombopoietin (TPO) receptor. Additionally, a therapeutically effective amount of a receptor binding moiety of the invention is administered to a subject in need of treatment for thrombocytopenia.

In a further aspect of the invention, the zinc chelated compounds of the invention are utilized as agonist of the leptin receptor. Additionally, a therapeutically effective amount of a receptor binding moiety of the invention is administered to a subject in need of treatment for obesity.

In a further aspect of the invention, the zinc chelated compounds of the invention are utilized as agonist of the interferon (IFN) alpha receptor. Additionally, a therapeutically effective amount of a receptor binding moiety of the invention is administered to a subject in need of treatment for hepatitis C.

In a further aspect of the invention, the zinc chelated compounds of the invention are utilized as agonist of the interferon (IFN) beta receptor. Additionally, a therapeutically effective amount of a receptor binding moiety of the invention is administered to a subject in need of treatment for multiple sclerosis.

In a further aspect of the invention, the zinc chelated compounds of the invention are utilized as agonist of the insulin receptor. Additionally, a therapeutically effective amount of a receptor binding moiety of the invention is administered to a subject in need of treatment for diabetes.

In a further aspect of the invention, the zinc chelated compounds of the invention are utilized as agonist of the tyrosine kinase (TRK) receptors. Additionally, a therapeutically effective amount of a receptor binding moiety of the invention is administered to a subject in need of treatment for CNS diseases.

In a further aspect of the invention, the zinc chelated compounds of the invention are utilized as dimeric cell-surface receptor agonist.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1
Preparation of Compound 1 Bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II)

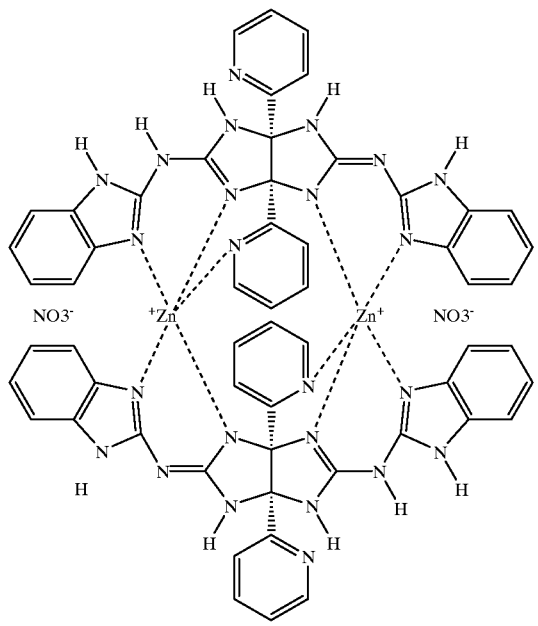

a)—Preparation of Compound 1a—2,5-Bis[2-benzimidazolylimino]-3a,6a-bis(2-pyridyl)-1,2,3,3a,4,5,6,6a-octahydroimidazo[4,5-d]imidazole A mixture of 2,2'-pyridil (15.8 g, 74.4 mmol) and 2-guanidinobenzimidazole (19.5 g, 111.7 mmol) in methanol (440 mL) was treated with a solution of sodium hydroxide (2.97 g, 74.4 mmol) in 74 mL and the resulting mixture was left standing at room temperature for 4 days. The crystalline material was filtered and dried under vacuum to yield 21.1 g of the title compound as off-white crystals (72%). mp: 305–307° C. (dec); HPLC retention time 4.5 min (reversed phase, Beckman ultrasphere ODS 4.6 mm×25 cm column, 20 min gradient elution with 20:80 to 60:40 acetonitrile:water containing 0.1% TFA @ 2 mL/min); $^1$H NMR (300 MHz, d$_6$-DMSO) d 11.5 (br s, NH, 2 H), 10.0 (br s, NH, 2 H), 8.6 (br s, NH, 2 H), 8.38 (d, J=4.2 Hz, 2 H), 7.55 (t, J=7.8 Hz, 2 H), 7.29 (d, J=7.8 Hz, 2 H), 7.27–7.21 (m, 4 H), 7.14 (br s, 2 H), 6.98 (dd, J=5.8, 3.2 Hz, 4 H); MS (ESI) m/z 527 [M+H]$^+$; Anal. Calcd. for C$_{28}$H$_{22}$N$_{12}$.2/3H$_2$O: C, 62.44; H, 4.37. N, 31.21; Found: C, 62.72; H, 4.08; N, 30.86.

b)—Preparation of Compound 1—Bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II)

A solution of compound from Example 1a (40 mg, 0.076 mmol) in 2 mL of 10% aqueous acetic acid was treated with a solution of zinc nitrate hexahydrate (24.9 mg, 0.0836 mmol) in water (1 mL). The mixture was left standing at room temperature for 6 h, and was then centrifuged, decanted and rinsed with water three times. The title compound was obtained as a white powder (13 mg). HPLC retention time 10.4 min (reversed phase, Beckman ultrasphere ODS 4.6 mm×25 cm column, 20 min gradient elution with 20:80 to 60:40 acetonitrile:water containing 0.1% TFA @ 2 mL/min); MS (ESI) m/z 1182 [M]$^+$, 591 [M]$^{++}$.

Example 2
Preparation of Compound 2—Bis{2,5-bis[2-benzimidazolylimino]-3a,6a-diphenyl-1,2,3,3a,4,5,6,6a-octahydroimidazo[4,5-d]imidazole-N,N'}-zinc(II)

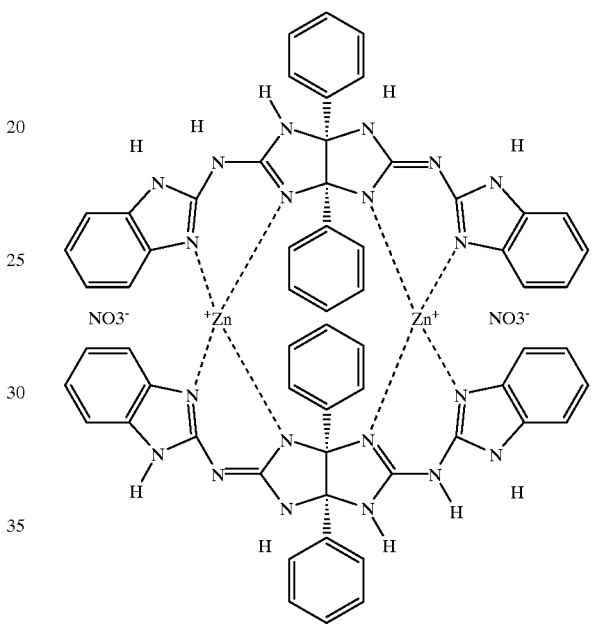

a)—Preparation of Compound 2a—2,5-Bis[2-benzimidazolylimino]-3a,6a-diphenyl-1,2,3,3a,4,5,6,6a-octahydroimidazo[4,5-d]imidazole A mixture of benzil (1.05 g 5.0 mmol) and 2-guanidinobenzimidazole (1.57 g, 9.0 mmol) in benzene (25 mL) was refluxed in pyridine (10 mL) for 1 h. After evaporating most of the pyridine under reduced pressure, the residue was treated with hot toluene and the resulting precipitate was filtered. The precipitate was then dissolved in 9:1 water:acetic acid (30 mL); the solution was filtered and the filtrate was neutralized to pH 7 with phosphate buffer. A precipitate formed, that was then collected and triturated with water to afford the title compound (0.42 g, 16%). $^1$H NMR (300 MHz, d$_6$-DMSO) d 11.5 (br s, NH, 2 H), 10.0 (br s, NH, 2 H), 8.6 (br s, NH, 2 H), 7.28–7.10 (m, 14 H), 6.97 (dd, J=6.0, 3.0 Hz, 4 H); MS (ESI) m/z 525 [M+H]$^+$; Anal. Calcd. for C$_{30}$H$_{24}$N$_{10}$.1/2CH$_3$CO$_2$H. 3/4H$_2$O: C, 65.37; H, 4.88; N, 24.65. Found: C, 65.36; H, 4.79; N, 24.48.

b)—Preparation of Compound 2—Bis{2,5-bis[2-benzimidazolylimino]-3a,6a-diphenyl-1,2,3,3a,4,5,6,6a-octahydroimidazo[4,5-d]imidazole-N,N'}-zinc(II)

A solution of compound from Example 2a (50 mg, 0.095 mmol) in 2 mL of methanol containing a drop of formic acid was treated with a solution of zinc nitrate hexahydrate (31.0 mg, 0.104 mmol) in methanol (1 mL). The mixture was left standing at room temperature for 18 h, and was then centrifuged, decanted and rinsed with water three times to yield the title compound as a white powder (35 mg). MS (ESI) m/z 1178 [M]$^+$, 589 [M]$^{++}$.

Example 3

Preparation of Compound 3 Bis{5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

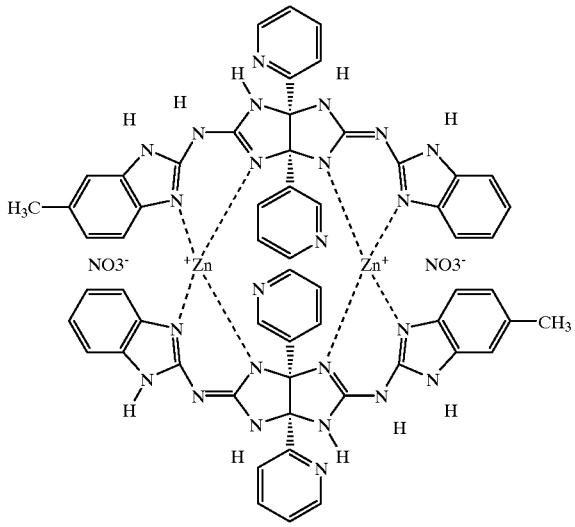

a) Preparation of Compound 3a—5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole bis(trifluoroacetate) salt A mixture of 2,2'-pyridil (135 mg, 0.636 mmol), 2-guanidinobenzimidazole (92.8 mg, 0.530 mmol) and 5-methyl-2-guanidinobenzimidazole (100 mg, 0.530 mmol) in methanol (3 mL) was treated with a solution of sodium hydroxide (38 mg, 0.95 mmol) in 0.5 mL of water and the resulting mixture was left standing at room temperature for 2 days. The crystalline material was filtered and purified by reversed phase preparative HPLC (Rainin Dynamax, 5 µM C18 column: 21.4 mm×25 cm, elution with gradient acetonitrile-water containing 0.1% trifluoroacetic acid) to yield the title compound as a white powder (88 mg, 18%). $^1$H NMR (300 MHz, d$_6$-DMSO) δ 13.0 (br s, NH, 4 H), 9.8 (br s, NH, 4 H), 8.39 (d, J=4.3 Hz, 2 H), 7.64 (td, J=7.8, 1.7 Hz, 2 H), 7.57 (d, J=7.8 Hz, 2 H), 7.49–7.46 (m, 2 H), 7.38–7.33 (m, 3 H), 7.27 (s, 1H), 7.21–7.13 (m, 3 H), 2.44 (s, 3 H); MS (ESI) m/z 541 [M+H]$^+$ b)—Preparation of Compound 3—Bis{5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

A solution of compound from Example 3a (70 mg, 0.091 mmol) in 10 mL of water was treated with a solution of zinc nitrate hexahydrate (40 mg, 0.136 mmol) in water (1 mL). The mixture was left standing at room temperature for 1 d, and was then centrifuged, decanted and rinsed with water three times. The title compound was obtained as a white powder (29 mg). HPLC retention time 11.8 min (reversed phase, Beckman ultrasphere ODS 4.6 mm×25 cm column, 20 min gradient elution with 20:80 to 60:40 acetonitrile:water containing 0.1% TFA @ 2 mL/min); MS (ESI) m/z 1210[M]$^+$, 605 [M]$^{++}$.

Example 4

Preparation of Compound 4—Bis{2,5-bis[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

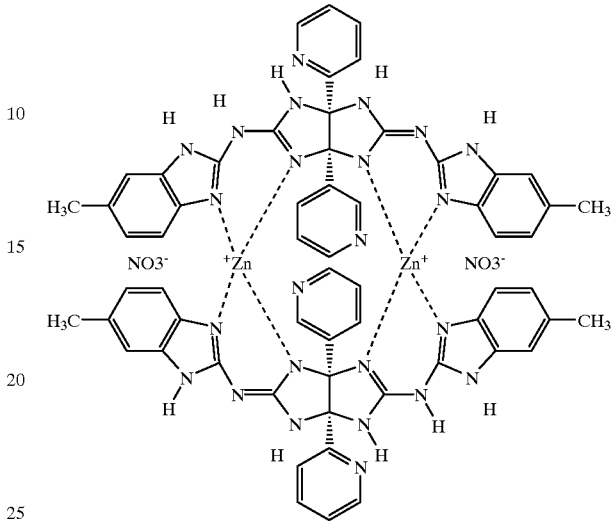

a) Preparation of Compound 4a—2,5-bis[(5-methyl-2-benzimidazolyl)imino]-3a,6a-bis(2-pyridyl)-1,2,3,3a,4,5,6,6a-octahydroimidazo[4,5-d]imidazole A mixture of 2,2'-pyridil (603 mg, 2.84 mmol) and 5-methyl-2-guanidinobenzimidazole (489 mg, 2.58 mmol) in methanol (17 mL) was treated with a solution of sodium hydroxide (113.6 mg, 2.84 mmol) in 2.8 mL of water. The title compound was isolated as a grey powder (450 mg, 63% yield). mp: 290–291° C. (dec); HPLC retention time 7.1 min (reversed phase, Beckman ultrasphere ODS 4.6 mm×25 cm column, 20 min gradient elution with 20:80 to 60:40 acetonitrile:water containing 0.1% TFA @ 2 mL/min); $^1$H NMR (300 MHz, d$_6$-DMSO) δ 11.3 (br s, NH, 2 H), 10.0 (br s, NH, 2 H), 8.5 (br s, NH, 2 H), 8.32 (d, J=4.2 Hz, 2H), 7.54(t, J=7.6Hz,2 H), 7.31 (d, J=7.6 Hz, 2H), 7.16 (d, J=7.8 Hz, 2 H), 7.16–7.09 (m, 2 H), 7.09 (s, 2 H), 7.14 (br s, 2 H), 6.86 (d, J=7.8, Hz, 2 H), 2.34 (s, 6 H); MS (ESI) m/z 555 [M+H]$^+$.

b)—Preparation of Compound 4—Bis{2,5-bis[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

A solution of compound from Example 4a (50 mg, 0.091 mmol) in 10 mL of water containing a few drops of formic acid was treated with a solution of zinc nitrate hexahydrate (40 mg, 0.136 mmol) in water (1 mL). The mixture was left standing at room temperature for 1 d, and was then centrifuged, decanted and rinsed with water three times. The title compound was obtained as a white powder (19 mg). HPLC retention time 13.3 min (reversed phase, Beckman ultrasphere ODS 4.6 mm×25 cm column, 20 min gradient elution with 20:80 to 60:40 acetonitrile:water containing 0.1% TFA @ 2 mL/min); MS (ESI) m/z 1238 [M]$^+$, 619 [M]$^{++}$.

Example 5

Capsule Composition

An oral dosage form for administering a presently invented agonist of the G-CSF receptor is produced by filing a standard two piece hard gelatin capsule with the ingredients in the proportions shown in Table I, below.

TABLE I

| INGREDIENTS | AMOUNTS |
| --- | --- |
| Bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II) (Compound 1) | 25 mg |
| Lactose | 55 mg |
| Talc | 16 mg |
| Magnesium Stearate | 4 mg |

Example 6

Injectable Parenteral Composition

An injectable form for administering a presently invented agonist of the G-CSF receptor is produced by stirring 1.5% by weight of 2,5-Bis[2-benzimidazolylimino]-3a,6a-diphenyl-1,2,3,3a,4,5,6,6a-octahydroimidazo[4,5-d]imidazole (Compound 2a) in 10% by volume propylene glycol in water.

Example 7

Tablet Composition

The sucrose, calcium sulfate dihydrate and a presently invented agonist of the G-CSF receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 2,5-Bis[2-benzimidazolylimino]-3a,6a-bis(2-pyridyl)-1,2,3,3a,4,5,6,6a-octahydroimidazo[4,5-d]imidazole (Compound 1a) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method for agonizing dimeric cell-surface receptors in a subject in need thereof which comprises administering to the subject a therapeutically effective amount of a zinc chelated dimeric cell-surface receptor ligand.

2. A method for agonizing dimeric cell-surface receptors in a subject in need thereof which comprises administering to the subject a therapeutically effective amount of an organic molecule having a molecular weight from about 100 to about 850, containing of from 1 to 4 zinc binding motifs and provided that each zinc binding motif forms at least two coordinate bonds to a zinc ion.

3. A method for identifying agonists of dimeric cell-surface receptors which comprises contacting the receptor with dimeric cell-surface receptor ligand candidates in the presence of a zinc ion source, and selecting ligand candidates which bind to the receptor.

4. A process for the preparation of a zinc chelated dimeric cell-surface receptor ligand which comprises reacting one or more receptor binding moieties and a zinc ion source followed by optional isolation of the zinc chelated dimeric cell-surface receptor ligand.

5. A zinc chelated cell-surface receptor ligand prepared by the process of claim 4.

6. A zinc chelated cell-surface receptor ligand.

7. A pharmaceutical composition comprising a pharmaceutically acceptable carrier and a compound of claim 5.

8. A pharmaceutical composition comprising a pharmaceutically acceptable carrier and a compound of claim 6.

9. A process for preparing a pharmaceutical composition containing a pharmaceutically acceptable carrier or diluent and an effective amount of a compound of claim 5 which process comprises bringing the compound into association with the pharmaceutically acceptable carrier or diluent.

10. A process for preparing a pharmaceutical composition containing a pharmaceutically acceptable carrier or diluent and an effective amount of a compound of claim 6 which process comprises bringing the compound into association with the pharmaceutically acceptable carrier or diluent.

11. An isolated dimeric cell-surface receptor binding moiety of a zinc chelated cell-surface receptor ligand.

12. A dimeric cell-surface receptor binding moiety.

13. The method of claim 1 wherein the cell-surface receptor is the EPO receptor.

14. The method of claim 2 wherein the cell-surface receptor is the EPO receptor.

15. A method for agonizing the EPO receptor in a subject in need thereof which comprises administering to the subject a therapeutically effective amount of a compound of claim 11.

16. A method for agonizing the EPO receptor in a subject in need thereof which comprises administering to the subject a therapeutically effective amount of a compound of claim 12.

17. A pharmaceutical composition comprising a pharmaceutically acceptable carrier and a compound of claim 11.

18. A pharmaceutical composition comprising a pharmaceutically acceptable carrier and a compound of claim 12.

19. A process for preparing a pharmaceutical composition containing a pharmaceutically acceptable carrier or diluent and an effective amount of a compound of claim 11 which process comprises bringing the compound into association with the pharmaceutically acceptable carrier or diluent.

20. A process for preparing a pharmaceutical composition containing a pharmaceutically acceptable carrier or diluent and an effective amount of a compound of a compound of claim 12 which process comprises bringing the compound into association with the pharmaceutically acceptable carrier or diluent.

21. A method for agonizing dimeric cell-surface receptors in a subject in need thereof which comprises administering to the subject a therapeutically effective amount of a compound of claim 11.

22. A method for agonizing dimeric cell-surface receptors in a subject in need thereof which comprises administering to the subject a therapeutically effective amount of a compound of claim 12.

23. A compound of claim 11 for use as an active therapeutic substance.

24. A compound of claim 12 for use as an active therapeutic substance.

25. The method of claim 1 wherein the dimeric cell-surface receptor is the M-CSF receptor.

26. The method of claim 2 wherein the dimeric cell-surface receptor is the M-CSF receptor.

27. A method for agonizing the M-CSF receptor in a subject in need thereof which comprises administering to the subject a therapeutically effective amount of a compound of claim 11.

28. A method for agonizing the M-CSF receptor in a subject in need thereof which comprises administering to the subject a therapeutically effective amount of a compound of claim 12.

29. The method of claim 1 wherein the dimeric cell-surface receptor is the GRH receptor.

30. The method of claim 2 wherein the dimeric cell-surface receptor is the GRH receptor.

31. A method for agonizing the GRH receptor in a subject in need thereof which comprises administering to the subject a therapeutically effective amount of a compound of claim 11.

32. A method for agonizing the GRH receptor in a subject in need thereof which comprises administering to the subject a therapeutically effective amount of a compound of claim 12.

33. The method of claim 1 wherein the dimeric cell-surface receptor is the TPO receptor.

34. The method of claim 2 wherein the dimeric cell-surface receptor is the TPO receptor.

35. A method for agonizing the TPO receptor in a subject in need thereof which comprises administering to the subject a therapeutically effective amount of a compound of claim 11.

36. A method for agonizing the TPO receptor in a subject in need thereof which comprises administering to the subject a therapeutically effective amount of a compound of claim 12.

37. The method of claim 1 wherein the dimeric cell-surface receptor is the leptin receptor.

38. The method of claim 2 wherein the dimeric cell-surface receptor is the leptin receptor.

39. A method for agonizing the leptin receptor in a subject in need thereof which comprises administering to the subject a therapeutically effective amount of a compound of claim 11.

40. A method for agonizing the leptin receptor in a subject in need thereof which comprises administering to the subject a therapeutically effective amount of a compound of claim 12.

41. The method of claim 1 wherein the dimeric cell-surface receptor is the IFN receptor.

42. The method of claim 2 wherein the dimeric cell-surface receptor is the IFN receptor.

43. A method for agonizing the IFN receptor in a subject in need thereof which comprises administering to the subject a therapeutically effective amount of a compound of claim 11.

44. A method for agonizing the IFN receptor in a subject in need thereof which comprises administering to the subject a therapeutically effective amount of a compound of claim 12.

45. The method of claim 1 wherein the dimeric cell-surface receptor is the insulin receptor.

46. The method of claim 2 wherein the dimeric cell-surface receptor is the insulin receptor.

47. A method for agonizing the insulin receptor in a subject in need thereof which comprises administering to the subject a therapeutically effective amount of a compound of claim 11.

48. A method for agonizing the insulin receptor in a subject in need thereof which comprises administering to the subject a therapeutically effective amount of a compound of claim 12.

49. The method of claim 1 wherein the dimeric cell-surface receptor is selected from the TRK receptors.

50. The method of claim 2 wherein the dimeric cell-surface receptor is selected from the TRK receptors.

51. A method for agonizing a selected TRK receptor in a subject in need thereof which comprises administering to the subject a therapeutically effective amount of a compound of claim 11.

52. A method for agonizing a selected TRK receptor in a subject in need thereof which comprises administering to the subject a therapeutically effective amount of a compound of claim 12.

53. The method of claim 1 wherein said metal chelated dimeric cell-surface receptor ligand comprises a symmetrical multimer of a receptor binding moiety.

* * * * *

UNITED STATES PATENT AND TRADEMARK OFFICE
CERTIFICATE OF CORRECTION

PATENT NO. : 6,280,959 B1
DATED : August 28, 2001
INVENTOR(S) : John G. Gleason and Juan I. Luengo Page 1 of 1

It is certified that error appears in the above-identified patent and that said Letters Patent is hereby corrected as shown below:

<u>Title page,</u>
Item [54], Title of application: "METAL COMPLEXES", should be -- NOVEL METAL COMPLEXES --.

<u>Column 16,</u>
Lines 56 through 59, claims 23 and 24, should be deleted.

Signed and Sealed this

Second Day of April, 2002

*Attest:*

JAMES E. ROGAN
*Attesting Officer*   *Director of the United States Patent and Trademark Office*